United States Patent [19]
Schenk

[11] Patent Number: 5,898,107
[45] Date of Patent: Apr. 27, 1999

[54] METHOD AND ARRANGEMENT FOR MONITORING THE OPERATION OF A HYDROCARBON SENSOR FOR AN INTERNAL COMBUSTION ENGINE

[75] Inventor: Rene Schenk, Tamm, Germany

[73] Assignee: Robert Bosch GmbH, Stuttgart, Germany

[21] Appl. No.: 08/923,930

[22] Filed: Sep. 5, 1997

[30] Foreign Application Priority Data

Sep. 7, 1996 [DE] Germany .......................... 196 36 415

[51] Int. Cl.⁶ .................................................. G01M 15/00
[52] U.S. Cl. .......................................... 73/118.1; 73/23.31
[58] Field of Search .............................. 73/23.31, 117.2, 73/118.1, 116, 117.3; 60/276; 123/688; 340/438

[56] References Cited

U.S. PATENT DOCUMENTS

| | | | |
|---|---|---|---|
| 4,175,427 | 11/1979 | Blanke ................................. | 73/118.1 |
| 4,419,190 | 12/1983 | Dietz et al. . | |
| 4,789,939 | 12/1988 | Hamburg .............................. | 73/118.2 |
| 5,105,651 | 4/1992 | Gutmann ............................... | 73/118.1 |
| 5,182,907 | 2/1993 | Kuroda et al. ....................... | 73/118.1 |
| 5,216,882 | 6/1993 | Kuroda et al. ........................ | 73/118.1 |
| 5,408,215 | 4/1995 | Hamburg .............................. | 73/118.1 |

OTHER PUBLICATIONS

"Automotive Handbook" published by Robert Bosch GmbH, (1993), pp. 164 to 167.

Primary Examiner—George Dombroske
Assistant Examiner—Eric S. McCall
Attorney, Agent, or Firm—Walter Ottesen

[57] ABSTRACT

The invention is directed to a method and an arrangement for monitoring the operation of a hydrocarbon sensor with which the sensor is monitored in a technically simple manner. The method and arrangement preferably utilize existing components of the motor vehicle. The heater power is continuously compared to a pregiven value. A sensor fault is signaled and the heater is shut off when the heater power and the pregiven value do not correspond to each other. The measured hydrocarbon value is compared to emission values to be expected for pregiven operating conditions and a sensor fault is signaled when the measured hydrocarbon value and the emission values do not correspond to each other.

10 Claims, 2 Drawing Sheets

Fig. 1

METHOD AND ARRANGEMENT FOR MONITORING THE OPERATION OF A HYDROCARBON SENSOR FOR AN INTERNAL COMBUSTION ENGINE

BACKGROUND OF THE INVENTION

High emissions of $NO_x$ occur in the exhaust gases in internal combustion engines which are driven with a high excess of air. This is especially true for internal combustion engines having direct injection into the combustion chamber. A reduction catalytic converter, for example, can be used for reducing these emissions. In order to reduce the $NO_x$, fuel is metered in additionally forward of the catalytic converter. This additional fuel is converted in the catalytic converter.

Furthermore, the exhaust gases of internal combustion engines of this type are after-treated via oxidation catalytic converters. In this way, the hydrocarbon (HC) emissions are significantly reduced.

In the United States, there has for some time been the requirement for monitoring the vehicle components and to display possibly occurring faults utilizing on board diagnosis (OBD).

Catalytic converters of internal combustion engines must also be monitored in the context of this on board diagnosis.

This occurs, for example, with hydrocarbon sensors (HC sensors).

Hydrocarbon sensors of this type essentially include a heater resistor and the actual sensor element. A temperature suitable for the measuring effect is adjusted with the aid of the heater resistor. It is necessary to measure the temperature because the temperature is to be adjusted via control. This takes place, for example, via the measurement of the internal resistance of the sensor element. This measurement is carried out with alternating current so that the direct-voltage signal of the probe remains essentially unaffected.

Such a temperature measurement is disclosed, for example, in U.S. Pat. No. 4,419,190 incorporated herein by reference.

Hydrocarbon sensors of this kind are used for monitoring and controlling exhaust-gas relevant components such as catalytic converters and/or metering pumps. For this reason, their function must also be monitored. If the sensor is defective, then, for example, the additional metering of fuel, which is dependent upon hydrocarbon emissions, must be switched off for an $NO_x$ catalytic converter.

SUMMARY OF THE INVENTION

In view of the above, it is an object of the invention to provide a method for monitoring the operation of a hydrocarbon sensor which makes possible monitoring the hydrocarbon sensor in a manner which is technically simple and uses already existing vehicle components.

The method of the invention is for monitoring the operation of a hydrocarbon sensor of an internal combustion engine. The hydrocarbon sensor supplies a sensor signal representing a measured hydrocarbon value and includes a heater wherein heater power is generated for heating said hydrocarbon sensor. The method includes the steps of: continuously comparing the heater power to a pregiven value; signaling a sensor fault and shutting off the heater when the heater power and the pregiven value do not correspond to each other; comparing the measured hydrocarbon value to emission values to be expected for pregiven operating conditions; and, signaling a sensor fault when the measured hydrocarbon value and the emission values do not correspond to each other.

The continuous monitoring of the heating power of the sensor affords the especially significant advantage that defective or interrupted sensor connections can be detected. If a sensor connection or a sensor line is interrupted, then the temperature can no longer be correctly detected or too low a value is continuously detected because an infinitely high internal resistance is usually assigned to room temperature. As a consequence, the sensor can be damaged by a heating power which is too high. This is avoided by continuously monitoring the heating power and comparing the same to a pregiven realistic value.

Furthermore, a defect of the sensor can be detected in a simple manner via the comparison of the detected sensor values for an intact heater with emission values of the engine, which are to be expected for pregiven operating conditions, and a fault of the sensor is signaled. This can, for example, take place in an advantageous manner in that the sensor value is compared to a pregiven base value of the sensor always when the vehicle, which contains the engine, is operated in overrun operation and when no additional fuel is metered in. A fault is indicated when this base value is exceeded. This is on the basis that the raw emissions of the engine are low in overrun operation of the vehicle (sometimes also at idle) and without metering additional fuel, so that the hydrocarbon value must perforce also be low.

If the base value is exceeded, then this can be caused, for example, by a defective sensor or a sensor coated with soot. For this reason, in an advantageous embodiment of the method of the invention, the heating power of the sensor is increased for a short time when the pregiven base value is exceeded and before a fault announcement is outputted in order to thereby permit the sensor to first burn off the soot.

In an advantageous embodiment of the invention, it is provided that a sensor fault is always signaled when the hydrocarbon value stays below a pregiven threshold within a pregiven time for an engine which is not operationally warm, while, at the same time, the injection quantity exceeds a pregiven threshold and the temperature of an exhaust-gas oxidation catalytic converter to be monitored lies below a pregiven threshold value in order to detect a sensor which is not sufficiently sensitive.

The threshold values are preferably determined by application.

In an advantageous embodiment, the heating power is continuously compared to a value taken from a characteristic field (map) for monitoring the heating power and, in the case where this value is exceeded, a sensor fault is signaled after a pregiven time span and the heater is switched off.

The arrangement of the invention is for monitoring the operation of a hydrocarbon sensor for an internal combustion engine. The hydrocarbon sensor supplies a sensor signal representing a measured hydrocarbon value and the hydrocarbon sensor has a heater. The arrangement includes: a first circuit part including: means for sensing the temperature of the hydrocarbon sensor; controller means for outputting an output signal to control the power of the heater in dependence upon the temperature; a characteristic field (map) for providing a threshold value (S1); a first comparator for comparing the output signal to the threshold; and, switchoff means for effecting a time delayed switching off of the heater when the signal and the threshold value (S1) do not correspond to each other; and, a second circuit part including: means for supplying emission values expected for pregiven operating conditions of the engine; a second comparator for comparing the hydrocarbon value to the emission values; and, means for outputting a fault signal indicating a fault when the hydrocarbon value does not correspond to the emission values.

As operating conditions of the engine, the following are used advantageously: the injection quantity, the metering of additional fuel and the temperature of a catalytic converter. These quantities are compared to pregiven thresholds in comparators.

The output of the fault signals preferably takes place, delayed in time, via time delay elements.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
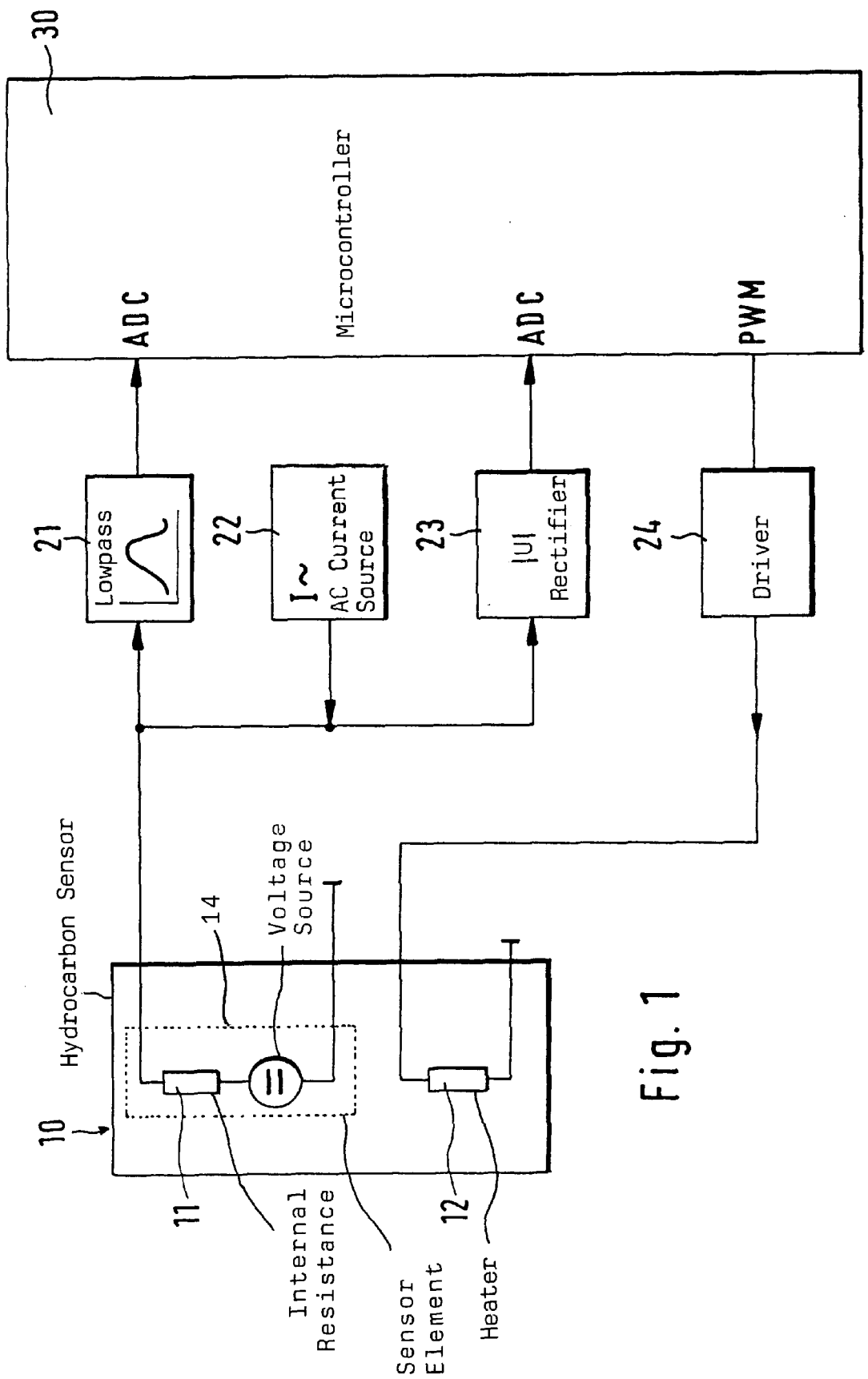
FIG. 1 shows schematically a hydrocarbon sensor connected to a microcontroller for driving and outputting the measured value; and, FIG. 2 is a block diagram of an arrangement according to the invention for monitoring the operation of a hydrocarbon sensor for a self-ignition internal combustion engine.

As shown in FIG. 1, a hydrocarbon sensor 10 includes a sensor element 14 as well as a heater 12. The evaluation circuit for the hydrocarbon sensor 10 is a control apparatus 30, for example, a microcontroller of an engine control apparatus. For measuring the temperature-dependent internal resistance 11 of the sensor element 14, an alternating-current source 22 is used as well as a rectifier 23 for the alternating voltage which adjusts because of the alternating current on the sensor element. The direct voltage signal of the probe, which represents the hydrocarbon value, remains uninfluenced with the use of an alternating current for determining the internal resistance of the sensor element. The actual measurement voltage is supplied via an analog/digital converter (ADC) to the control apparatus 30 by a lowpass 21 which separates the measurement alternating voltage provided for temperature determination. The lowpass 21 is a $PT_1$ element (first order time-delay element). In this connection, reference can be made to the text "Automotive Handbook" published by Robert Bosch GmbH (1993), pages 164 to 167.

A temperature control algorithm is provided for heating the hydrocarbon sensor 10. The temperature control algorithm generates a pulsewidth modulated signal (PWM) which is supplied to a driver 24 from the control apparatus 30. The driver 24, in turn, drives the heater 12.

Figure 2:
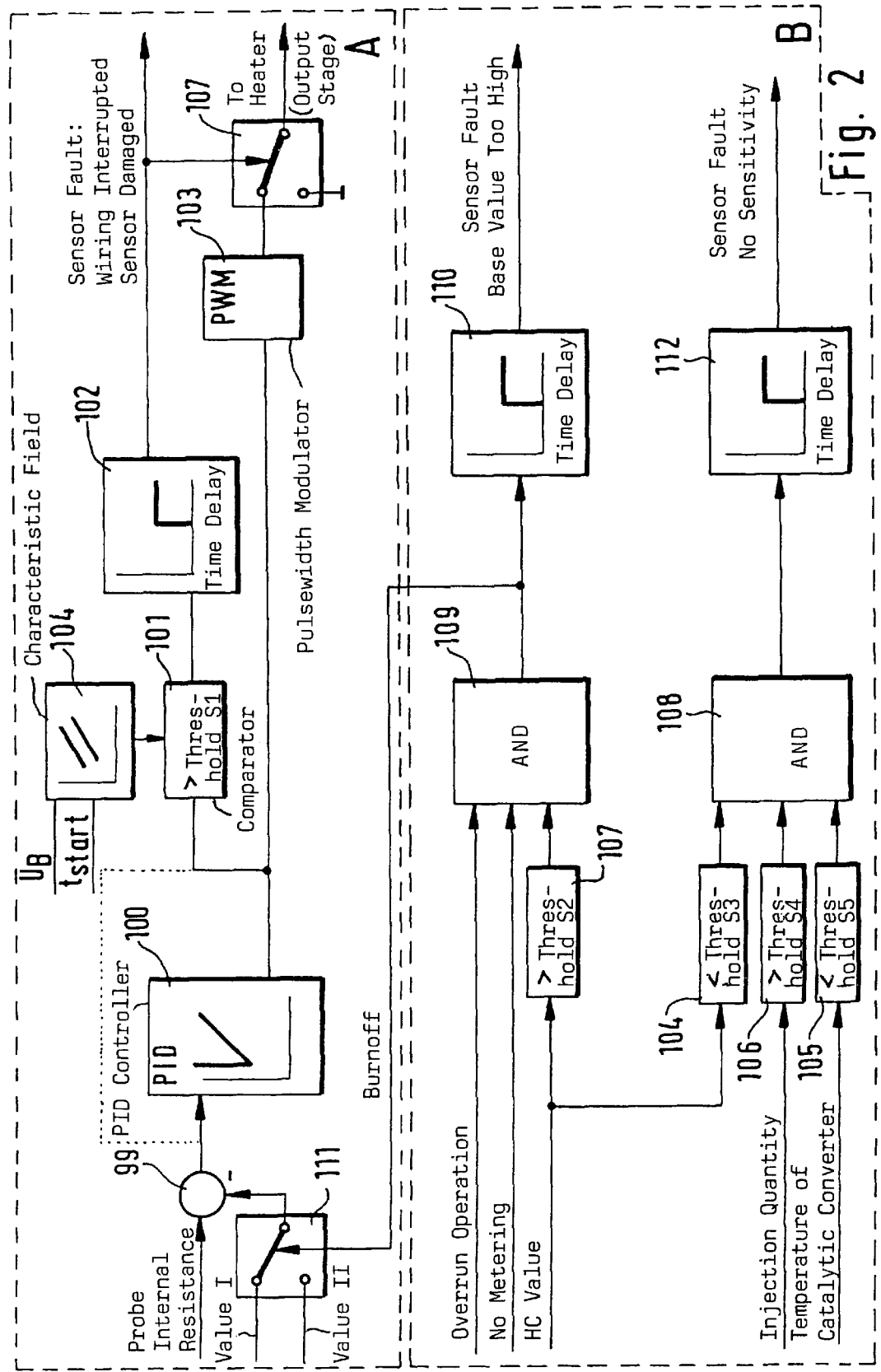

The method for monitoring the operation of the hydrocarbon sensor 10 for a self-igniting internal combustion engine is best explained with respect to FIG. 2. FIG. 2 schematically shows an arrangement for monitoring the operation of the hydrocarbon sensor.

As shown in FIG. 2, the arrangement for monitoring the operation of the hydrocarbon sensor 10 includes a first circuit part A. The circuit part A, in turn, includes a controller 100 for the control of the heating power via a pulsewidth modulator (PWM) 103 in dependence upon the detected temperature of the sensor. The controller 100 can, for example, be a PID controller.

For this purpose, a pregiven value I is subtracted in a subtractor 99 from the detected probe internal resistance and supplied to the controller 100. The value I corresponds to a pregiven probe internal resistance for a normal operating temperature. The signal outputted by the controller 100 is compared to a pregiven threshold value S1 in a comparator 101. The threshold value S1 is taken from a characteristic field or map 104. The input quantities of the characteristic field 104 are essentially the on-board voltage UB as well as the time tstart which has elapsed since the start of the engine. If the value, which is outputted by the controller 100, is greater than the threshold value S1, a sensor fault is outputted and, at the same time, a further heating of the hydrocarbon sensor 10 takes place. However, if the heater power exceeds the threshold S1 longer than a pregiven time span (which is realized by the delay element 102), then the case is present that, for example, the sensor terminals are interrupted or the sensor 10 is damaged. In this case, a sensor fault is signaled and the heater is switched off by a switch 107.

In a second circuit part B, the detected sensor values are compared to emission values, which are expected for pregiven operating conditions, and, for the case where matching is not present, a fault of the sensor 10 is signaled.

For this purpose, it is, for example, detected whether the sensor 10 exceeds a pregiven hydrocarbon value (HC-value) in the overrun operation of the vehicle (that is, without fuel injection and without metering of additional fuel into the exhaust gas). This takes place via a comparison of the measured HC-value in a comparator 107 to a threshold value (threshold) S2. If this is the case, then a fault signal is outputted in the logic and 109. This leads to the output of a sensor fault (for example, of the content "base value too high") after passing a delay element 110.

At the same time, the input value I is switched to the input value II via a switch 111 via a signal line. The input value II leads to an increased heating power and so to a burnoff of the sensor via the temperature control described in connection with the circuit part A.

This burnoff takes place only for a short time. The time is especially shorter than the time span pregiven by the delay element 110 so that, for a soot-coated sensor, the sensor fault "base value too high" is no longer signaled after the burnoff when no other sensor defect is additionally present.

In another branch of the circuit part B, a determination is made in a comparator 104 as to whether the HC-value is less than a pregiven threshold S3 when, at the same time, the injection quantity exceeds a pregiven threshold S4, which is determined in comparator 106, and the catalytic converter temperature stays below another pregiven threshold value S5 which is determined in the comparator 105. Since all above-mentioned conditions are satisfied, a fault signal is outputted in the logic and 108 which, after passing a time-delay element 112, leads to a sensor fault having, for example, the content "no sensitivity".

The last-described fault monitoring always takes place after a cold start, that is, when the catalytic converter still has so low a temperature for a time that the raw emissions of the engine are not converted. In this time, an HC sensor which is mounted downstream of the catalytic converter, must measure a high value. The temperature downward of the catalytic converter can then be either measured or can be computed utilizing a model. The threshold S5, to which the catalytic converter temperature is compared in the comparator 105, corresponds essentially to the start temperature of the catalytic converter.

It is a significant advantage that the entire circuit arrangement is part of an engine control known per se so that, in this manner and without additional hardware, sensor faults and therefore also catalytic converter faults can be detected on board, that is, with on board means.

It is understood that the foregoing description is that of the preferred embodiments of the invention and that various changes and modifications may be made thereto without departing from the spirit and scope of the invention as defined in the appended claims.

What is claimed is:

1. A method for monitoring operation of a hydrocarbon sensor of an internal combustion engine, the hydrocarbon sensor supplying a sensor signal representing a measured hydrocarbon value and including a heater wherein heater power is generated for heating said hydrocarbon sensor, the method comprising the steps of:

continuously comparing said heater power to a pregiven value;

signaling a sensor fault and shutting off said heater when said heater power and said pregiven value do not correspond to each other;

comparing said measured hydrocarbon value to emission values to be expected for pregiven operating conditions; and, signaling a sensor fault when said measured hydrocarbon value and said emission values do not correspond to each other.

2. The method of claim 1, wherein said engine is in a motor vehicle; and, wherein a fault announcement is outputted when said measured hydrocarbon value exceeds a pregiven hydrocarbon value and when said vehicle is driven in overrun operation and when no additional fuel is metered to said engine.

3. The method of claim 2, comprising the further step of increasing said heating power for a short time when said pregiven hydrocarbon value is exceeded.

4. The method of claim 1, wherein, for an engine not operationally warm, a sensor fault is always signaled when:

said measured hydrocarbon value stays below a pregiven threshold value (S3) within a pregiven time;

at the same time, an injection quantity exceeds a pregiven further threshold (S4); and, at the same time, the temperature of a catalytic converter to be monitored is below still another pregiven further threshold (S5).

5. The method of claim 4, wherein said thresholds are determined by adaptation.

6. The method of claim 1, wherein said sensor fault is signalled after a time delay.

7. The method of claim 1, comprising the further steps of:

comparing said heater power to a value taken from a characteristic field; and, signaling a fault and switching off said heater when said heater power exceeds said value within a pregiven time span.

8. An arrangement for monitoring operation of a hydrocarbon sensor for an internal combustion engine, said hydrocarbon sensor supplying a sensor signal representing a measured hydrocarbon value and said hydrocarbon sensor having a heater, the arrangement comprising:

a first circuit part including:

means for sensing the temperature of said hydrocarbon sensor;

controller means for outputting an output signal to control power of said heater in dependence upon said temperature;

a characteristic field or map for providing a threshold value (S1);

a first comparator for comparing said output signal to said threshold; and, switchoff means for effecting a time delayed switching off of said heater when said signal and said threshold value (S1) do not correspond to each other; and, a second circuit part including:

means for supplying emission values expected for pregiven operating conditions of said engine;

a second comparator for comparing said hydrocarbon value to said emission values; and, means for outputting a fault signal indicating a fault when said hydrocarbon value does not correspond to said emission values.

9. The arrangement of claim 8, wherein said engine includes a catalytic converter; and, wherein said pregiven operating conditions include: a quantity of fuel injected; a metering of additional fuel; and, the temperature of said catalytic converter; and, said second circuit part further including: a plurality of thresholds for said operating conditions; and, a plurality of comparators for receiving said thresholds, respectively, and for comparing said operating conditions to corresponding ones of said thresholds.

10. The arrangement of claim 8, wherein said second circuit part includes time-delay elements for delaying the output of said fault signal.

* * * * *